United States Patent [19]
Che et al.

[11] Patent Number: 5,604,587
[45] Date of Patent: Feb. 18, 1997

[54] LONG CAPILLARY WAVEGUIDE RAMAN CELL

[75] Inventors: Diping Che; Su-Yi Liu, both of Sarasota, Fla.

[73] Assignee: World Precision Instruments, Inc., Sarasota, Fla.

[21] Appl. No.: 559,560

[22] Filed: Nov. 16, 1995

[51] Int. Cl.$^6$ ..................................................... G01N 1/10
[52] U.S. Cl. ........................ 356/246; 356/338; 356/339; 356/343
[58] Field of Search ..................................... 356/246, 336, 356/338, 339, 340, 343

[56] References Cited

U.S. PATENT DOCUMENTS

| | | |
|---|---|---|
| 4,690,560 | 9/1987 | Coogan ..................................... 356/236 |
| 5,134,445 | 7/1992 | Toge ........................................ 356/246 |
| 5,485,270 | 1/1996 | Freud et al. ............................. 356/246 |

*Primary Examiner*—Frank Gonzalez
*Assistant Examiner*—Reginald A. Ratliff
*Attorney, Agent, or Firm*—Chilton, Alix & Van Kirk

[57] ABSTRACT

The chemical properties of an aqueous liquid, the liquid comprising a solvent having an index of refraction which is the same as or closely approaches that of water, are determined by Raman spectroscopy wherein a sample of the liquid is delivered into an optical waveguide. The waveguide is in the form of a capillary having a reflective surface defined by a material having a refractive index of less than 1.33. Excitation light is transmitted axially into the liquid at an end of the waveguide. The excitation light is transmitted the length of the waveguide, by reflection from the reflective surface, causing the fluid to emit Raman spectra. The Raman spectra is transmitted along the waveguide, collected and delivered to a spectrometer.

23 Claims, 5 Drawing Sheets

LONG CAPILLARY WAVEGUIDE RAMAN CELL

FIELD OF THE INVENTION

The present invention relates to the detection of analytes present in an aqueous solution and particularly to the performance of light spectrum measurements to determine the chemical properties of a liquid analyte. More specifically, this invention is directed to analytical cells configured for Raman spectroscopy which employ a liquid core waveguide as the cell in which fluid analyte is placed while being illuminated by a monochromatic light whereby line spectrum induced in the analyte may be measured. Accordingly, the general objects of the present invention are to provide novel and improved methods and apparatus of such character.

BACKGROUND OF THE INVENTION

The irradiation of certain sample materials with an intense monochromatic light causes pertubations of the molecular energy levels of the sample. As a result, secondary light waves with wavelengths which are different than that of the monochromatic light are produced and radiated from the sample. This phenomenon is known as Raman scattering.

Raman spectroscopy is a well established technique that enjoys wide application in industry and many fields of research. However, Raman scattering is a very weak effect. Consequently, conventional Raman spectroscopy requires a highly focused and intense laser beam and a very efficient detection system. Typically, Raman light is collected from a point source, within a small solid angle.

In 1972, Stone and Walrafen demonstrated that the use of a liquid core waveguide can enhance the Raman signal detected from a sample by a factor of $10^2$ to $10^3$. This improvement resulted from using a sample solution as the core and the cell wall as the waveguide cladding. Accordingly, both the excitation light and the Raman light are guided along the waveguide/cell and thus through the liquid sample. Increasing the length of the tubing increases the number of interactions between the excitation light and the sample solution, thereby magnifying the Raman signal. Stone and Walrafen used quartz tubing as their cell and were unable to measure Raman spectra in fluids having refractive indices equal to or lower than the refractive index of quartz (1.46). Restated, the described technique relied upon reflection from the interface between the sample/core and the cell wall and the requisite reflection, in turn, requires that there be an interface between the core and a material having a lower index of refraction, In 1987, Schwab and McCreery disclosed a long capillary Raman cell consisting of uncoated glass tubing exposed to air. Total reflection theoretically occurred at the glass/air interface on the exterior surface of the tubing. With a refractive index of 1.0, the air total reflection surface virtually removed the constraint on the refractive index of the liquid sample. However, this design is subject to several limitations. The excitation light intensity is almost evenly distributed within the total diameter of the cell. Consequently, the cell wall must be very thin to retain effective excitation intensity within the sample. Therefore, cells in accordance with this design are exceedingly fragile and are likely to break when subjected to a slight amount of flexing. Furthermore, the outside of the cell must be kept extremely clean in order to maintain efficient waveguide action.

Due to the above-discussed limitations of the previously proposed apparatus, the liquid core waveguide method for intensifying Raman signals has not been exploited. The failure to exploit this technology can be primarily attributed to the unavailability of an appropriate material with which to construct a commercially viable aqueous waveguide cell.

SUMMARY OF THE INVENTION

The present invention overcomes the above-briefly discussed and other deficiencies and disadvantages of the prior art by providing a Raman cell having a long path length. This invention thus also encompasses a method of achieving the enhancement of Raman light signals.

In accordance with a preferred embodiment of the present invention, a suitably shaped vessel, i.e., a waveguide, is fabricated from a glass or quartz which has been coated on a surface with a material having a refractive index lower than that of water (1.33). Alternatively, the vessel may be fabricated from a material having a refractive index lower than 1.33.

The vessel or cell described above acts as a waveguide when filled with an aqueous solution or any other liquid which has a refractive index which is greater than that of the coating. The excitation light radiation is confined within the sample liquid and the cell wall by means of the total reflection surface defined by the coating. Typically, the cell will be in the form of a capillary tube. Within a finite cone, Raman emission in forward and backward directions relative to the excitation propagation is integrated over the length of the capillary.

A Raman cell in accordance with the present invention intensifies the Raman light signal for aqueous samples. Additionally, a Raman cell in accordance with the present invention is more flexible, sturdier and easier to use than conventional Raman cells.

BRIEF DESCRIPTION OF THE DRAWING

The present invention may be better understood and its numerous objects and advantages will become apparent to those skilled in the art by reference to the accompanying drawings wherein like reference numerals refer to like elements in the several figures and in which.

DETAILED DESCRIPTION OF THE DISCLOSED EMBODIMENTS

Figure 1:
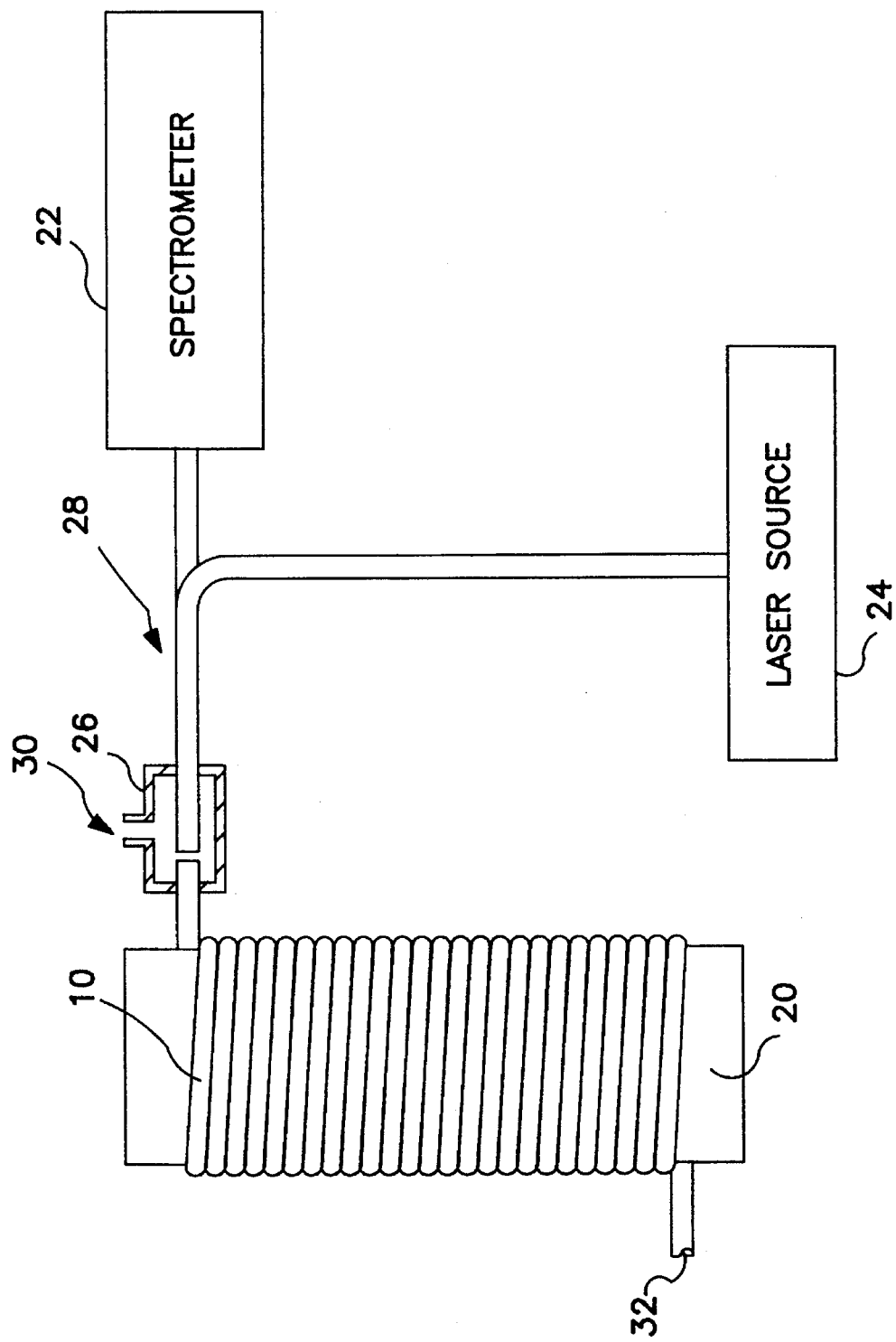
FIG. 1 is a schematic view of a first embodiment of a Raman spectrometer employing a cell in accordance with the invention.

In the practice of the present invention, a liquid core waveguide is employed as the sample cell of a Raman spectrometer. In order to propagate light therethrough with negligible losses, it is necessary that the core region of a waveguide/cell in accordance with the invention effectively be surrounded by a material having a lower refractive index to the incident light than the liquid material comprising the core. This arrangement results in most of the light which seeks to escape through the wall of the light conductor being reflected from the interface at the core side of the low refractive index material and, therefore, confined within the core region provided, of course, that the incident light is transmitted into the core material within an appropriate acceptance angle relative to the axis of the core.

As discussed above, the use of an aqueous liquid as the core material has heretofore been impractical because of limitations in the materials which defined the surface from which the reflection occurred and/or the materials which comprised the body of the waveguide. In the practice of the present invention, a waveguide 10 is constituted by a suitably shaped vessel 12, for example a capillary, for containing a liquid core 14, i.e., an aqueous sample. Capillary 12 may be fabricated from glass, quartz, transparent polymers such as polymethyl methacrylate (PMMA), polyvinylidene fluoride (PVDF) and ethylene tetrafluoroethylene (ETFE), or similar materials.

A material which possess a refractive index which is less than 1.33 may be used to clad a surface of the capillary 12. Materials usable for cladding the interior surface 16 of the capillary 12 must be non-reactive and insoluble in water. Suitable amorphous polymers with sufficiently low refractive indices can be created if their structural elements include some or all of the fluorocarbon groups —$CF_3$, —$CF_2O$, —$CF(CF_3)_2$ and —$CH(CF_3)_2$. A commercially available fluorocarbon material having a refractive index which is suitable for use in the practice of the present invention is sold by the Dupont Company under the trademark "Teflon AF". This commercially available fluorocarbon material has a refractive index in the range of approximately 1.29 to 1.31 and is insoluble in water.

In accordance with the preferred embodiment, the total reflection surface is located at the exterior surface of capillary 12. Thus, the outer surface of capillary 12 is clad with, for example, an inorganic material having a very low index of refraction. These materials may be soluble in the core liquid. Appropriate exterior cladding materials, in addition to the preferred fluorocarbon materials described above, include beryllium fluoride glasses such as $BeF_2$, Be-RbF, $BeF_2$—KF, $BeF_2$—LiF, $BeF_2$—NaF, and fluorophosphate glasses. An arrangement wherein reflection of excitation light occurs at the exterior surface 18 of capillary 12 also allows the interior surface 16 of the capillary to be modified to reduce the adhesion or retention of molecules in the liquid due to surface potential. For example, a silanization procedure may be used to change the charge on the interior surface 16 from negative to neutral or positive.

Figure 5:
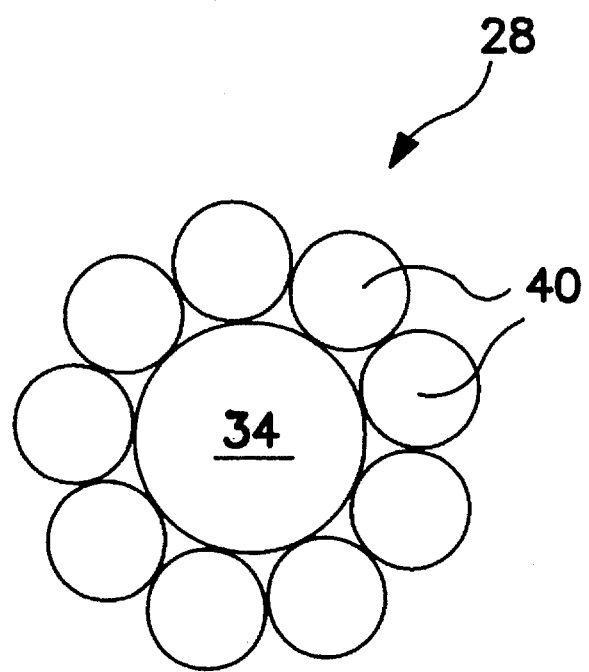
FIG. 5 is a cross-sectional view, taken along line 5—5 of FIG. 1, of the fiber optic bundle of the apparatus of FIG. 1.

Referring to FIG. 1, the waveguide/cell 10 of a Raman spectrometer comprises a length of tubing defining a capillary 12 which may be wound around a cylindrical form 20 for convenience. The capillary 12 is optically coupled to a spectrometer 22 in the manner to be described below, and to a laser excitation light source 24. This coupling is accomplished by means of a coupler which is indicated generally at 26. The excitation light source 24 typically produces light having wavelengths in the range of 400 nm to 900 nm. The coupler 26 includes an optical fiber bundle 28 as shown in FIG. 5. Fluid samples are introduced into the cell, i.e., into capillary 12, via an orifice 30 in the coupler 26 and the gap between the end of capillary 12 and the end of fiber optic bundle 28. The width of this gap is minimized to that which will allow air to escape from the capillary 12 as the fluid sample is introduced. Fluid may exit the cell via a discharge "port" 32.

Preferably, light for excitation is supplied via optical fiber 34 located at the center of bundle 28. The axis of excitation fiber 34 is aligned with the axis 36 of the capillary 12 (see FIG. 3) to efficiently couple the excitation light into the cell. For proper operation, the excitation light is transmitted exclusively into the liquid sample 14. Such action is required because, in the embodiment of FIGS. 1—3, the refractive index of the capillary 12 is smaller than that of the exterior cladding 38 and the liquid sample 14. If the excitation radiation directly enters the capillary wall, it may be trapped inside the capillary wall by means of total reflection at the two opposite surfaces 16, 18. The remaining optical fibers 40 of bundle 28 collect the Raman emissions and deliver the thus collected light to spectrometer 22.

Figure 2:
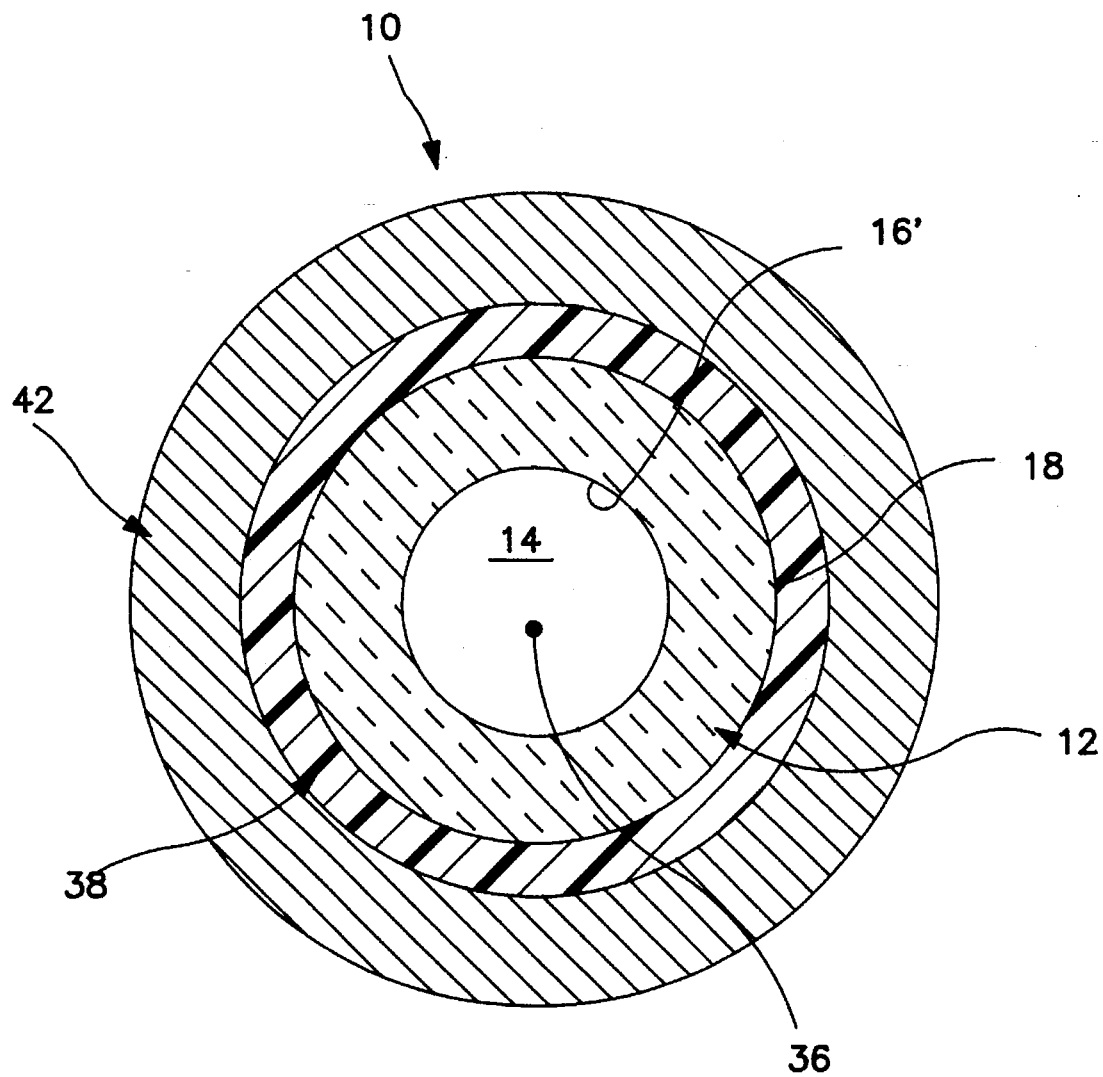
FIG. 2 is a cross-sectional view of the waveguide/cell of FIG. 1.
Figure 3:
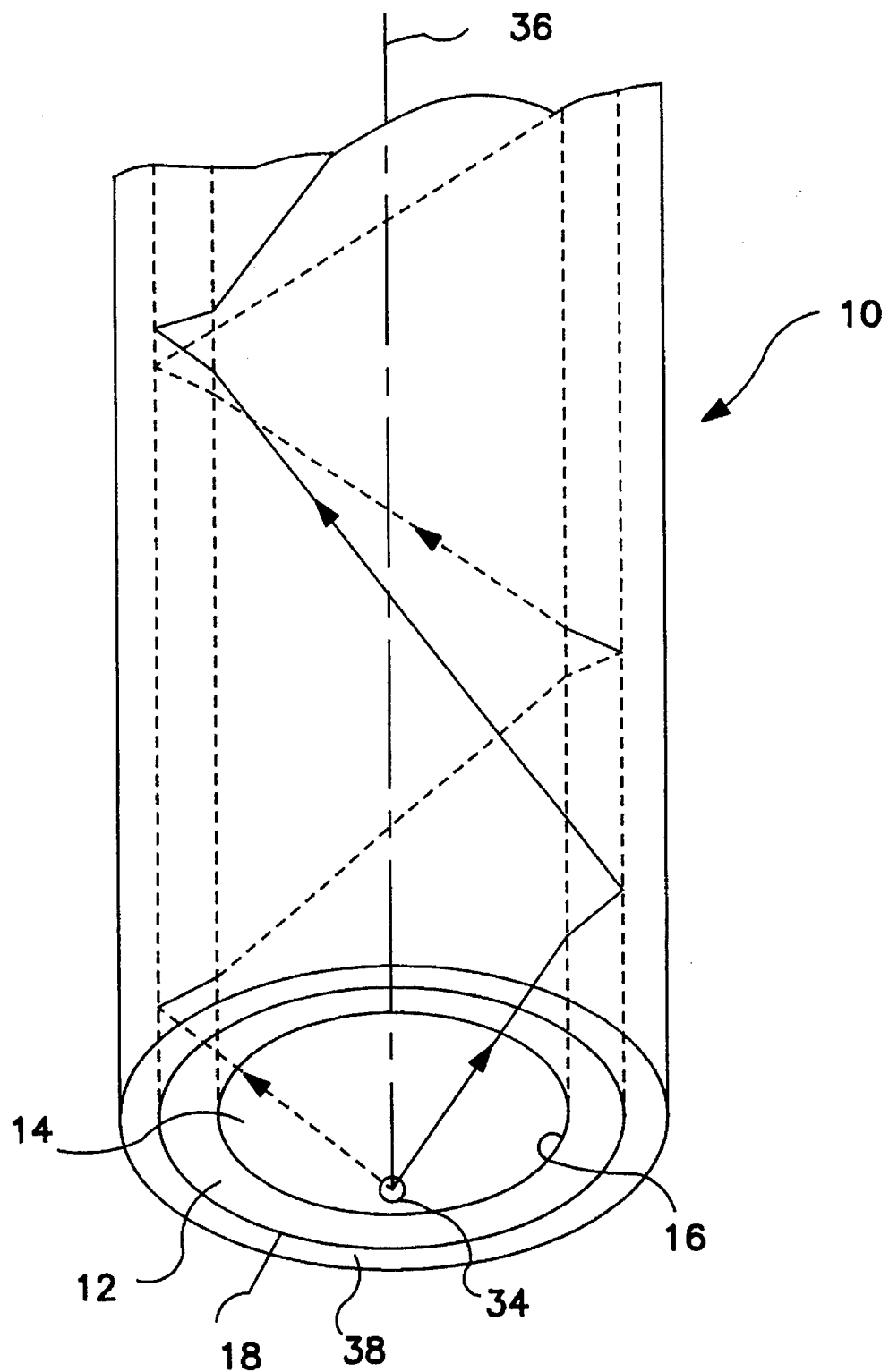
FIG. 3 is a schematic showing which illustrates the mode in which the waveguide of FIG. 1 functions.

As shown in FIG. 2, the waveguide 10 is comprised of a long capillary 12 clad with a polymer material 38 having a refractive index lower than that of the sample liquid. The capillary wall and the sample liquid 14 together constitute the core. The cladding 38 should have a thickness of at least four (4) times the wavelength of the light to be propagated by the waveguide, i.e., a cladding thickness of 2 μm to 3.6 μm is appropriate, and may be applied by dipping, spraying or other means known in the art.

The cladding 38 is preferably applied immediately after the capillary wall is drawn. The cladding 38 protects the capillary from degradation due to light, moisture, oxidation and environmental contaminants. Such degradation typically causes the capillary to become brittle. Therefore, a Raman cell manufactured in accordance with the present invention is more flexible than conventional Raman cells. For example a Raman cell manufactured in accordance with the present invention may be wound into a three inch coil.

Since capillary 12 supports the disclosed circular cross-sectional shape of the cell, the physical strength requirement for the cladding material is reduced. A protective outer coating or jacket 42 of stainless steel or other suitable material may be employed to protect the cladding material from scratching and mechanical abrasion.

The following relation determines the conical zones within which the excitation and Raman emission are transmitted through the cell:

$$\theta_5 < \sin^{-1} \frac{n_{14}}{n_{38}}$$

where θ is the angle of incidence with the interior surface of the capillary and $n_{14}$ and $n_{38}$ denote refractive indices of the liquid sample and the cladding, respectively. Light energy is evenly distributed within this cone over the cross section of the capillary 12 and liquid sample 14 by means of successive transmission and reflection. Therefore, the capillary wall should be thin relative to the capillary diameter so that most of the excitation energy is distributed within the liquid sample 14. This distribution does not affect the collection of Raman emission if the fiber bundle 28 is large enough to accept the light output from both the core liquid 14 and the capillary wall.

Figure 4:
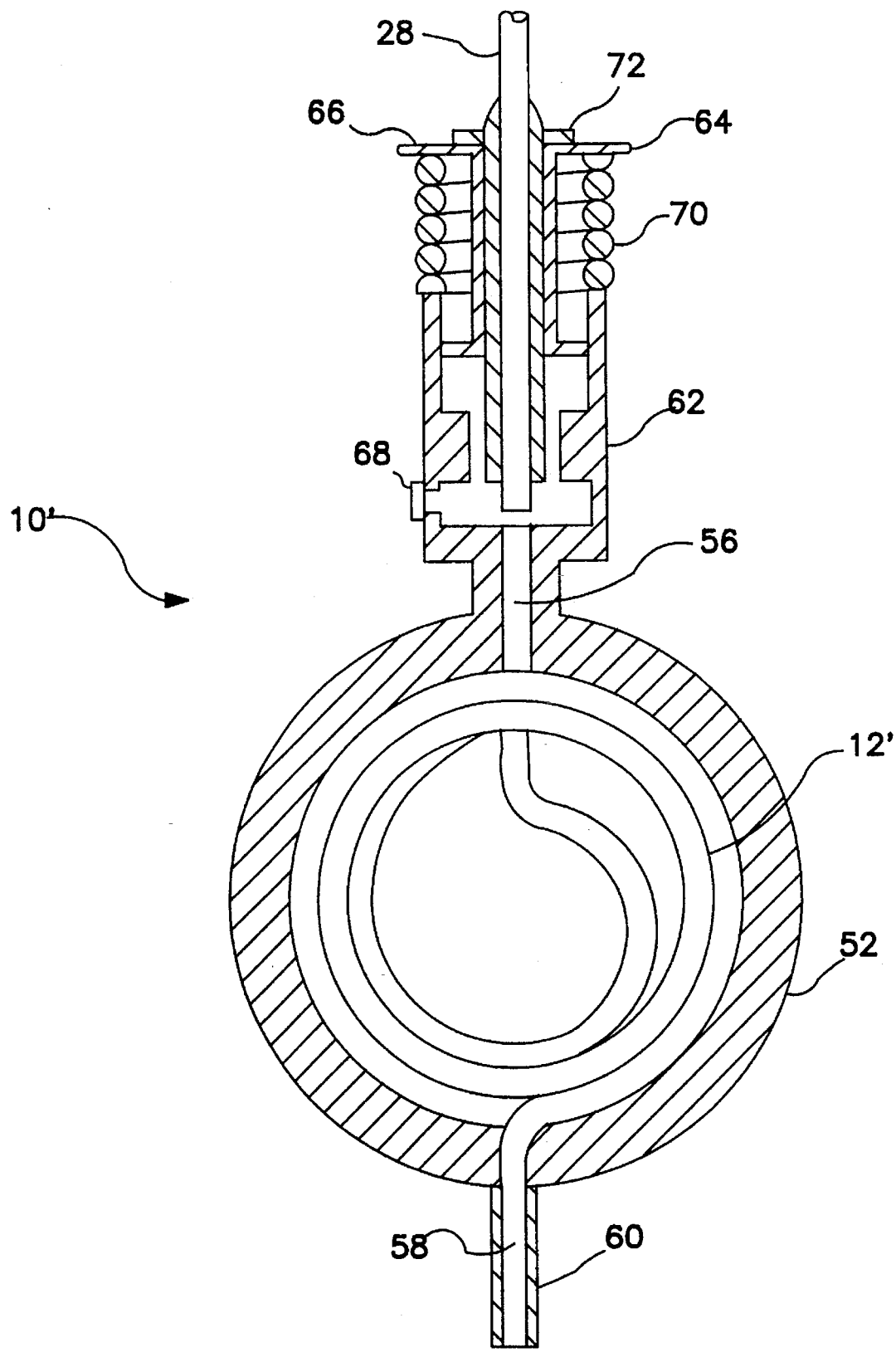
FIG. 4 is a cross-sectional view of a second embodiment of a Raman cell for use in the practice of the invention.

An alternative embodiment is shown in FIG. 4. This embodiment has the advantage of being compact and convenient. The FIG. 4 arrangement is best suited for a Raman cell with a relatively small inner diameter which in turn allows a small coil diameter. The capillary body 12' of the cell 10', which preferably has the same construction as depicted in FIG. 2, is coiled inside a rigid protective cover 52. The radius of the coil should be large enough to insure that bending light loss is minimal. Generally, the bending radius is a function of the numerical aperture of the excitation light delivery fiber and the diameter of the fiber. In a preferred embodiment, the bending radius is approximately equal to 100 times the cladding diameter. A first end portion 58 of the capillary body 12' extends outside of the cover 52. The first end portion 58 is shielded by a rigid and chemically inert sleeve 60. The second end portion 56 of the capillary body 12' is coupled to the fiber optic bundle 28 by means of a coupler/pipetter 62.

The liquid sample may be drawn into the capillary 12' by immersing the open end of the capillary in the sample solution, closing the valve 68 and then releasing the end 66 of piston 64. A spring 70 biases the end 66 of the piston 64 away from the capillary 12' to create a suction which draws the sample into the capillary. A stop 72 prevents the piston 64 from being pushed out of the coupler/pipetter 62. Valve 68 provides a means of quickly changing the pressure inside coupler 62 and capillary 12'.

As an alternative to the use of a cladding on capillary 12, as described above, the capillary may itself be constructed of Teflon AF.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A cell for use in the measurement of the chemical properties of aqueous samples containing dissolved analytes by Raman spectroscopy, said cell comprising:

capillary tube means having a wall which defines interior and exterior surfaces, said tube means having an elongated inner central region for receiving a sample to be analyzed, at least that part of said capillary tube means which is in direct communication with said central region being non-reactive with the sample, said tube means being capable of being flexed without significantly varying the cross-sectional shape of said central region said capillary tube means further having first and second ends which determine the length of the measurement cell, said capillary tube means defining a reflection surface for confining light energy within said capillary tube means, the portion of said tube means situated to the interior of said reflection surface comprising a light transmitting core which includes said central region whereby light energy may be transmitted from the first end of said capillary tube means to said second end of said capillary tube means, irradiation light energy launched into and transmitted through said core causing Raman scattering in the sample whereby light with wavelengths different from said irradiation light wavelength is produced by interaction between said irradiation light and the sample, said different wavelengths being commensurate with a line spectrum which identifies constituents of the analytes;

means for coupling irradiation light energy into said core via said capillary tube means first end whereby a liquid sample in said core region may function as a light conducting medium in an aqueous liquid core wavelength; and light receiving means positioned adjacent one of said ends of said capillary tube means for receiving at least a portion of the Raman scattering light produced by interaction between said irradiation light and the sample in said core region, said Raman scattering light being reflected to said light receiving means by said reflection surface.

2. The cell of claim 1 wherein said capillary tube means comprises a capillary tube and cladding means on at least one surface of said tube, said cladding means having a refractive index which is less than 1.33.

3. The cell of claim 2 wherein said coupled light energy has a wavelength and said cladding means has a thickness equal to at least four times said wavelength.

4. The cell of claim 3 wherein said cladding means is disposed on said exterior surface of said tube.

5. The cell of claim 4 wherein said tube is comprised of a material selected from the group comprising glass, quartz and transparent polymers and wherein said cladding means comprises a layer of material selected from the group comprising an amorphous solid fluorocarbon material, a beryllium fluoride glass and fluorophosphate glass.

6. The cell of claim 3 wherein said cladding means is disposed on said interior surface of said tube and comprises a layer of an amorphous solid fluorocarbon material.

7. The cell of claim 5 wherein said tube has a silanization process treatment of said interior surface.

8. The cell of claim 5 further comprising jacket means disposed around said cladding means for protecting said cladding means from degradation.

9. The cell of claim 1 wherein said capillary tube means is comprised of a fluorocarbon material having a refractive index in the range of 1.29 to 1.31.

10. The cell of claim 1 further comprising coupler means, said first end of said capillary tube means being disposed within said coupler means, said coupler means providing fluid communication to said core region of said capillary tube means.

11. The cell of claim 10 wherein said means for transmitting and said light receiving means each comprise at least one optical fiber, said optical fibers defining a bundle having an end, said bundle extending into said coupler means, said end of said bundle and said first end of said capillary tube means defining a gap, fluid communication with said core of said capillary tube means being established via said gap.

12. The cell of claim 11 wherein said first end of said capillary tube means defines a first axis and said means for transmitting defines a second axis, said second axis being substantially aligned with said first axis.

13. The cell of claim 1 wherein fluid communication between an external fluid source and said central region of said capillary tube means is established via said capillary tube means second end whereby a fluid to be analyzed may be drawn into and discharged from said capillary tube means central region via said second end.

14. The cell of claim 13 further comprising means for imparting movement to a fluid to be analyzed, and movement imparting means being fluidically coupled to said central region.

15. The cell of claim 14 wherein said means for transmitting comprises an optical fiber and said light receiving means comprises at least one optical fiber, said optical fibers defining a bundle and terminating at a first end of said bundle, said fluid motion imparting means piston means including a bore for receiving said first end of said bundle, said piston means bore being disposed in registration with said first end of said capillary means.

16. The cell of claim 15 wherein said piston means further comprises an engagement portion and spring means, said spring means biasing said engagement portion away from said first end of said capillary means.

17. The cell of claim 16 wherein said piston means further comprises valve means for changing the piston means pressure.

18. In a method for the optical detection of an analyte present in an aqueous fluid by Raman Spectroscopy, the improvement comprising the steps of:

delivering an aqueous liquid sample containing at least a first dissolved analyte into a waveguide capillary having first and second ends which are fluidically opposed, said ends defining the length of an open-ended measurement cell, said cell including a wall having interior and exterior surfaces, said interior surface surrounding an open central region of substantially circular cross-section, said wall at least in part being formed of a layer comprised of a material having a refractive index of less than 1.33, said layer being of substantially annular shape and being coaxial with said central region, the delivered sample being disposed in the cell central region whereby the sample comprises a light transmitting core of the cell;

coupling a source of irradiation light to a first end of the capillary waveguide central region whereby light from the source will be launched into the sample and guided along the length of the cell by reflection from an interface between said material having a refractive index of less than 1.33 and material having a greater refractive index, the coupled light causing Raman scattering in the sample whereby secondary light waves with wavelengths which are different than that of the mean wavelength of the irradiation light are produced;

receiving at least a portion of the emitted secondary light waves at one of the ends of the capillary; and analyzing the received light.

19. The method of claim 18 wherein the source of light energy comprises an optical fiber having an axis and the core of the capillary defines an axis, the step of coupling includes aligning the axis of the optical fiber with the axis of the core region at the first end of the capillary.

20. The method of claim 19 wherein the step of receiving includes positioning the first end of at least one optical fiber adjacent to and in registration an end of the open central region of the capillary.

21. The method of claim 20 further comprising the step of placing the waveguide capillary within a protective jacket.

22. The method of claim 18 wherein the material having a refractive index of less than 1.33 comprises a cladding of a fluorocarbon material on the exterior surface of a thin walled, substantially transparent capillary tube, said tube and cladding cooperating to define the measurement cell wall.

23. The method of claim 22 wherein the step of coupling comprises selecting a light source which provides monochromatic light having a wavelength which is less than ¼ the thickness of said cladding.

* * * * *